(12) United States Patent
Lowell et al.

(10) Patent No.: US 6,292,687 B1
(45) Date of Patent: Sep. 18, 2001

(54) MEDICAL EMERGENCY RESPONSE AND LOCATING SYSTEM

(76) Inventors: DeWitt James Lowell, 6622 138th Pl. SW., Edmonds, WA (US) 98026-3234; Rulon R. Dahl, 103 N. Donlee, #3, St. George, UT (US) 84770

( * ) Notice: Subject to any disclaimer, the term of this patent is extended or adjusted under 35 U.S.C. 154(b) by 0 days.

(21) Appl. No.: 09/658,080

(22) Filed: Sep. 11, 2000

Related U.S. Application Data

(60) Provisional application No. 60/207,479, filed on May 25, 2000.

(51) Int. Cl.[7] ............................................. A61B 5/026
(52) U.S. Cl. ................................................. 600/515
(58) Field of Search ..................... 607/5, 6, 32; 600/515, 600/518

(56) References Cited

U.S. PATENT DOCUMENTS

| | | |
|---|---|---|
| 4,819,860 | 4/1989 | Hargrove et al. . |
| 4,909,260 | 3/1990 | Salem et al. . |
| 5,002,060 | 3/1991 | Nedivi . |

(List continued on next page.)

OTHER PUBLICATIONS

Baker, Stephen et al., "The Wireless Internet", *Business Week*, May 29, 2000, 136–144, McGraw–Hill Companies.
Wildstrom, Stephen H., "Can Oxygen Turn Sci–Fi Into Reality?", *Business Week*, Jul. 17, 2000, 22 and 24, McGraw–Hill Companies.
"MIT Project Oxygen", http://www.oxygen.lcs.mit.edu/, Jul. 24, 2000, 5 pages.
Emery, Theo, "Researchers aim to make computers vanish", http://seatletimes.nwsource.com/news/nation–world/html98/comp22_20000622.html, Jun. 24, 2000, 2 pages.
"Motorola Bluetooth (Bluetooth in Action)"; http://www.mot.com/bluetooth/action/action.html; Sep. 2, 2000, 5 pages + 1 page.

*Primary Examiner*—Scott M. Getzow
(74) *Attorney, Agent, or Firm*—Mallinckrodt & Mallinckrodt; Robert R. Mallinckrodt

(57) ABSTRACT

An emergency response system for detecting, locating, and responding to a predetermined medical emergency, such as sudden cardiac arrest/sudden cardiac death, in a person being sensed for the predetermined emergency, and wherein the medical emergency can be treated with portable medical equipment, such as an AED machine for treating cardiac arrest/sudden cardiac death, includes a reader worn by the person being sensed for reading a dysfunction indicating the existence or imminent existence of the emergency condition and a sensor for determining when an emergency condition is read and producing an alarm signal. A processor activates a personal alarm at the location of the person suffering the emergency, now the victim, which indicates the emergency and the victim's location to those in the victim's immediate area. The processor also transmits an alarm signal to an alarm indicator on the portable medical equipment to alert anyone in the immediate area of the equipment, an emergency response person, that a victim is in immediate need of such equipment. Preferably, the alarm signal includes location signals which indicate the location of the victim to direct the emergency response person with the equipment to the victim. The processor preferably also transmits or causes transmission of an alarm signal to a remote emergency response center which receives the alarm and dispatches an emergency response person or emergency response team to the victim. Again, location information in or with the alarm signal directs the emergency response person to the location of the victim. The invention provides a closed loop system, i.e., victim emergency, transmission of alarm signal and location information to an emergency response person, and response by an emergency response person to the victim.

48 Claims, 3 Drawing Sheets

U.S. PATENT DOCUMENTS

Figure 1:
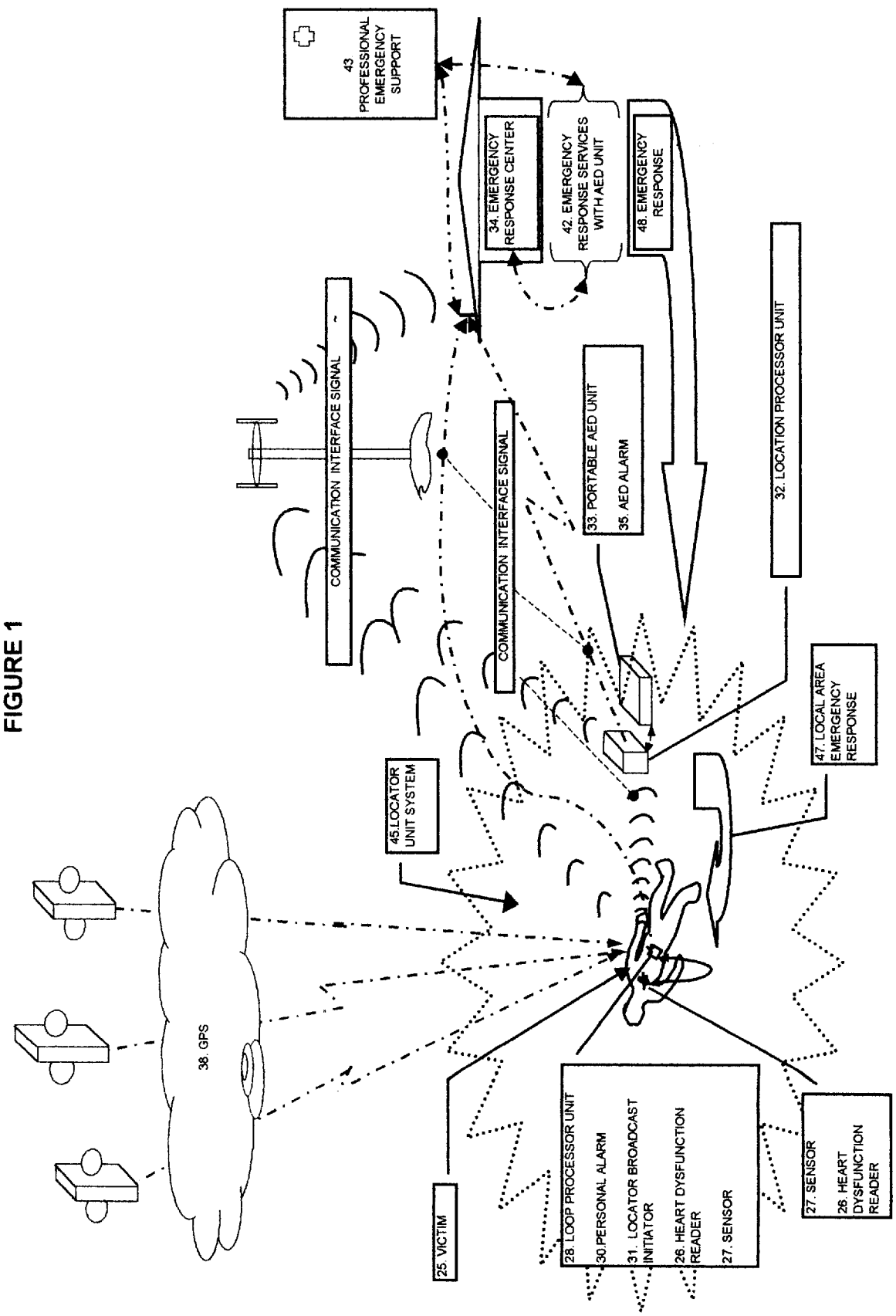

| | | |
|---|---|---|
| 5,157,604 | 10/1992 | Axford et al. . |
| 5,228,449 * | 7/1993 | Christ et al. . |
| 5,319,355 | 6/1994 | Russek . |
| 5,630,209 | 5/1997 | Wizgall et al. . |
| 5,652,570 | 7/1997 | Lepkofker . |
| 5,712,619 | 1/1998 | Simkin . |
| 5,752,976 | 5/1998 | Duffin et al. . |
| 5,782,878 * | 7/1998 | Morgan et al. . |
| 5,835,061 | 11/1998 | Stewart . |
| 5,966,692 | 10/1999 | Langer et al. . |
| 5,969,678 | 10/1999 | Stewart . |
| 6,073,046 | 6/2000 | Patel et al. . |
| 6,083,248 | 7/2000 | Thompson . |

\* cited by examiner

MEDICAL EMERGENCY RESPONSE AND LOCATING SYSTEM

This application claims the benefit of provisional application Ser. No. 60/207,479, filed May 25, 2000, entitled "Cardiac Arrest Indentification And Response System".

BACKGROUND OF THE INVENTION

1. Field

The invention is in the field of medical emergency detection and response systems.

2. State of the Art

In the United States today there are approximately 400,000 incident congestive heart failure patients who are at extreme risk of sudden cardiac arrest/sudden cardiac death or heart attack, and about five million prevalent patients who are at high risk. About 350,000 people a year in the United States die from some type of cardiac arrest/sudden cardiac death. One of the main causes of sudden cardiac arrest/sudden cardiac death is the arrhythmia termed ventricular fibrillation. The quivering ventricles suspend the ability of the heart to act as a hemodynamic transfer pump thus stopping blood flow in the body. Without blood flow, various organs of the body, and especially the brain, are deprived of oxygen and glucose. When deprived of oxygen and glucose, the brain will start to loose both its cognitive ability or capability and its stimulative and integrative functions. The extent of this brain loss is time dependent becoming mostly irreversible after five minutes, and with possible total loss of brain function usually between seven and eight minutes. For every minute that elapses after normal blood flow ceases, the chance of survival diminishes by seven to ten percent. Survival rates for people who suffer sudden cardiac arrest/sudden cardiac death outside of a hospital are estimated to be as low as 1.4 percent. Thus, quick response to the loss of heart beat is critical if a patient is to survive and be functional. The use of CPR is merely a first aid response that usually buys only a few minutes for the person whose heart is beating erratically.

The AED or automatic external defibrillator is a device or machine to stop ventricular fibrillation and has been perfected to be used by individuals who are not medically trained. Usually these individuals are locally trained in the use of the AED machine. Thus, police and fire personnel, security officers, and lay persons with some background can effectively use currently available AED's. As AED's further develop, their use will be more and more simplified. AED machines are currently available that can be operated by untrained persons by merely reading simple instructions on the AED or listening to voice instructions generated by the AED during use. The major problems, however, are the recognition of the need to defibrillate (use the AED) and the response time to get an AED machine to a person in need of defibrillation once the need is recognized. In recognizing the need, the person suffering the need has to be noticed. Generally such person will fall to the ground from lack of muscular response. The person is noticed by spectators or bystanders, called a witnessed event, who eventually recognize that a problem exists. A telephone call to 911 or other emergency service is made and the journey to the scene by the emergency response personnel begins. While many emergency response agencies tout a three to four minute response time, this time is from when they are notified of the emergency. If two or three minutes have already passed before such agency receives notice of the emergency, the three or four minute response time is not fast enough.

Compounding the problem is the finding that at least thirty five percent of persons suffering sudden cardiac arrest/sudden cardiac death and maybe as high as seventy to eighty percent are unwitnessed, such as at night or when a person is not at home or unwitnessed in hospitals or nursing homes. Such persons may often be beyond any hope of revival by the time they are discovered.

There is currently a move in the United States to make AED's more available and accessible. The Government is planning to place AED's in public buildings such as airports and Federal buildings, and local communities are similarly attempting to make AED's available in public places and in police cars. A major US airlines is joining three foreign airlines in placing an AED on each of its aircraft. A life was reported saved shortly thereafter as a result. However, even with increased availability of AED's, detection and recognition of those needing treatment is critical. Further, being able to find an AED machine if one is located nearby is also critical.

Various monitoring systems have been proposed to monitor persons, such as persons having implanted medical devices, for among other things, emergency medical situations. For example, U.S. Pat. No. 6,083,248 assigned to Medtronic, Inc. discloses a system for monitoring and reprogramming implanted medical devices such as heart pacemakers and pacemaker-cardioverter-defibrillator combinations. The system transmits signals representative of operation of the monitored device to a medical support network or location which can remotely keep track of the operation of the implanted device and can remotely reprogram the device. The system also keeps track of the location of the person with the device through various locating systems such as a global positioning system (GPS) or other known system. The described system can also alert emergency medical personnel upon detection of an emergency situation and guide such emergency medical personnel to the person involved. However, although such system monitors implanted heart devices and detects heart conditions, the alarm indications are sent to the medical support network, which may be remote from the victim, and response time remains a problem. This response time is a problem even in notification through a 911 network which is contemplated by the patent. Various other monitoring systems such as shown in U.S. Pat. No. 6,073,046, also have similar problems.

SUMMARY OF THE INVENTION

According to the invention, a person to be monitored for a cardiac arrest/sudden cardiac death condition wears a heart dysfunction reader that detects a heart dysfunction indicating imminent or occurring cardiac arrest/sudden cardiac death. For example, for occurring cardiac arrest/sudden cardiac death, the heart dysfunction reader can detect the presence of a pulse, beating of the heart, heart rhythms, or the presence of blood flow in the body. This can be done in various ways by various types of known detectors such as pulse detectors, heartbeat detectors, heart rate monitors, or rhythm sensors. A sensor recognizes an emergency condition (a cardiac arrest/sudden cardiac death condition) indicated by information read by the heart dysfunction reader and initiates the system resulting in the giving of an alarm to indicate the cardiac arrest/sudden cardiac death condition in the person sensed, now the victim. The alarm not only indicates that the victim needs immediate help, but also provides immediate information of the victim's location so that not only is an immediate alarm provided to start the emergency response, but response is aided by the alarm's helping to quickly locate the victim. The location information is preferably provided by at least a personal audio or visual alarm associated with the victim so that the victim is immediately identified to all those in the immediate area of the victim, i.e., within earshot of the alarm on the victim or in position to see the victim, as well as by a remote alarm such as at the nearest AED location and\or at a remote emergency response center such as police, fire, or paramedic location which also provides victim location information. With the immediate alarm and location information, immediate response is begun in a closed loop fashion, i.e., alarm from the victim to response person and response from response person to victim.

In a preferred system of the invention, AED units are situated at various locations, particularly in and around public places such as airports, office and civic buildings, apartments or other high density residential buildings, and in places such as parks, as well as in private residential or non-public places. The AED units each have an AED alarm on or associated with the unit so that a victim's emergency condition activates the victim's personal alarm and the alarm at the AED location. This means that a response person, who can be any person who becomes aware of the alarm, will have help both in finding the victim who needs immediate help and in finding an AED machine to use in providing the immediate help to the victim. In addition, if, as preferred, the alarm signal is also sent to an emergency response center, which could be the location of the AED machine, a response person from an emergency response service is also dispatched to the victim. This helps ensure a rapid and satisfactory response to the emergency situation.

In addition to the audio or visual alarm provided at the victim location and preferably at the AED location (the alarm at the victim location giving an indication of the location of the victim to those in the immediate area), the alarm signals preferably also include additional location signals such as global positioning satellite signals (GPS signals) or other signals which pinpoint the location of the victim when response personnel are receiving the alarm at a response location distant from the victim or at the AED machine when the AED machine is located outside the immediate area of the victim. Such location signals may be generated by a local network of location signal producing devices, such as transmitters, with a transmitter in each room of a building or in various positions in public or common areas, which transmit location signals to the system of the invention which retransmits such signals with or as part of the alarm signal. These location signals will direct the response persons to the specific location of the victim such as to the victim's house or to an office building or other location where the audio and/or visual alarm associated with the victim then helps in the immediate specific locating of the victim. In one embodiment of the system of the invention, an audio alarm associated with the victim is initially relatively soft to alert only persons near the victim of the emergency condition and an alarm at the location of the AED machine is relatively loud to alert anyone in a more distant area around the AED machine that an emergency condition exists. Upon a response person obtaining the AED machine, the alarm at the location of the AED, such as on the AED itself, becomes relatively soft or stops and the alarm associated with the victim increases in volume and becomes relatively loud to aid the person with the AED in finding the victim.

Since the victim may be in a locked home or building and may be in a darkened room, the system can be arranged so that upon transmittal of the alarm signal, building and room locks are unlocked to allow access to the victim by emergency response persons and lights in a darkened room are turned on or can be set to go on and off. The lights will help locate the victim to an emergency response person.

It may generally be desirable to provide an alarm reset switch in the portion of the system worn by the person being sensed so if the alarm is activated in what the person being sensed can determine is obviously a false alarm, the person being sensed can reset and quiet the system. Such situation may arise, for example, if the person being sensed takes off the heart dysfunction reader so that it correctly reads a lack of detection of a heart function, but falsely reads this lack of heart function as an alarm situation.

More generally, the invention contemplates an emergency response system for detecting, locating, and responding to predetermined medical emergencies in a person being sensed for such emergencies wherein the emergency is one that can be effectively treated with portable medical equipment that can be placed at various locations in the general vicinity of the person being sensed's normal areas of activities, such as in the vicinity of the person's residence and in the vicinity of the person's work. If the system detects a predetermined medical emergency condition in the person being sensed, a personal alarm is activated to alert those in the immediate area of the person being sensed of the emergency and a transmitter transmits an emergency signal. The emergency signal is received by an equipment alarm on any, or at least the closest, item of portable medical equipment in the vicinity of the person being sensed to alert those in the area of the equipment that a person is in need of the equipment. Depending upon the locations of the equipment, the equipment alarm preferably also provides location information regarding the victim's location to guide the person with the equipment to the victim. This location information may be provided by various location indicating systems such as a locator unit system or GPS locator system or a local transmitter system and the emergency signals include location signals, such as GPS signals or other location indicating signals received at the victim's location. The emergency signal may also be received at an emergency response center which sends an emergency response person to the victim, again using location information provided by the location signals transmitted with the emergency signals.

For purposes of the invention, the victim being sensed is not limited to a human being, but may also include an animal, such as a pet.

THE DRAWINGS

Figure 2:
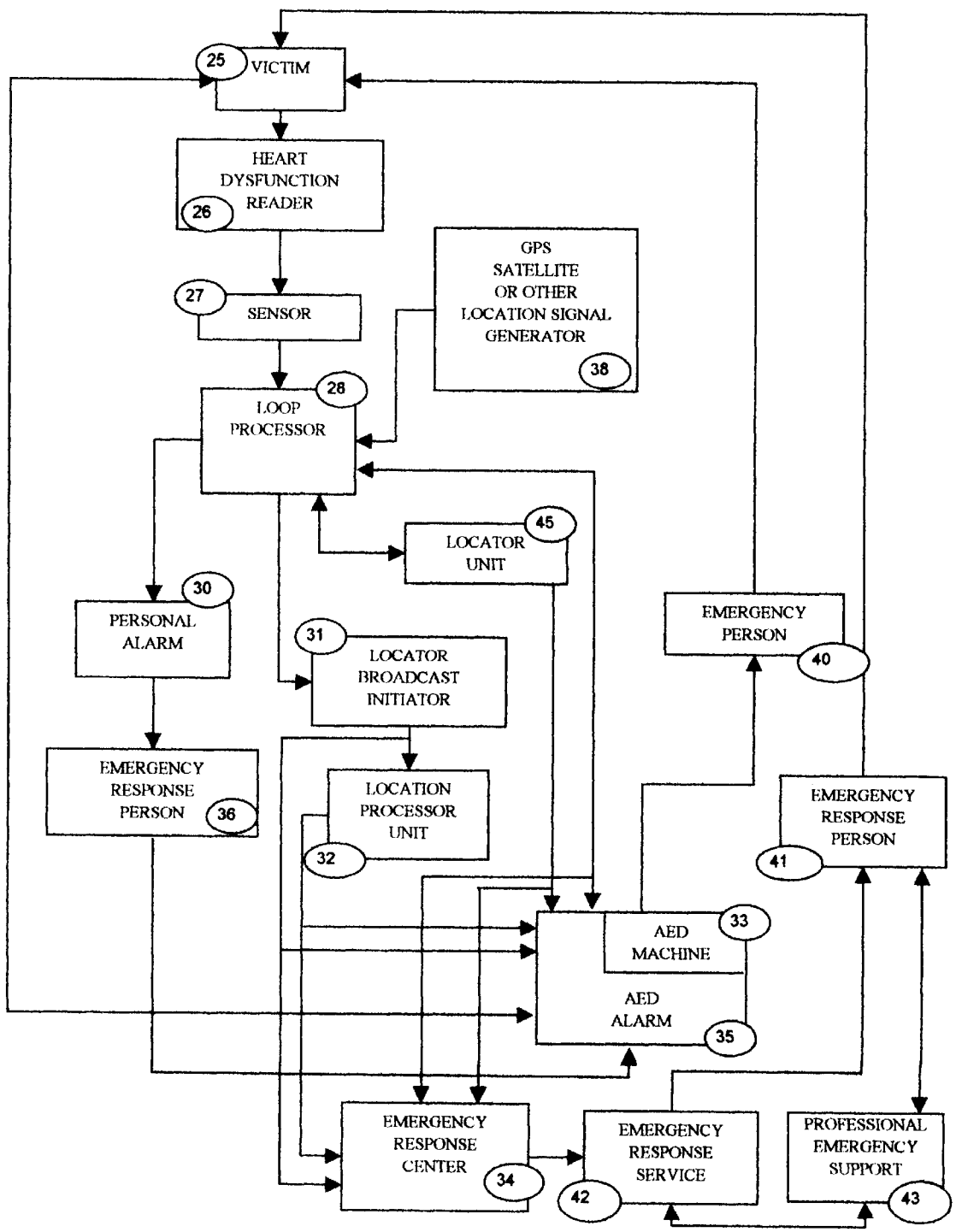

The best mode presently contemplated for carrying out the invention is illustrated in the accompanying drawings, in which:

FIG. 1 is a diagrammatic showing of the system of the invention;

FIG. 2, a block diagram of the system of FIG. 1; and

Figure 3:
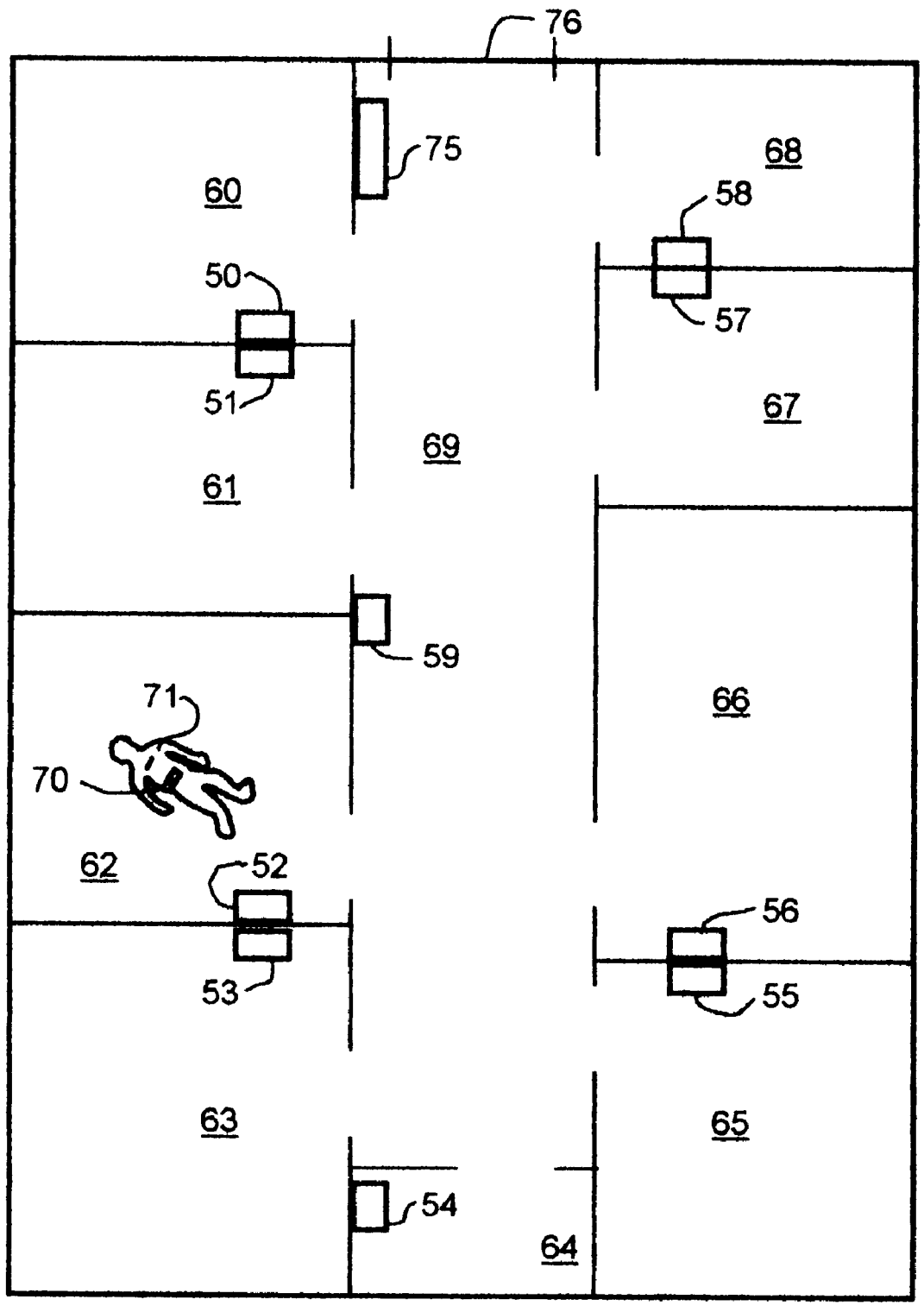

FIG. 3, a schematic diagram of a building floor plan showing location of local address transmitters in each room and a victim in one room.

DETAILED DESCRIPTION OF THE ILLUSTRATED EMBODIMENT

The system of the invention is shown diagrammatically by FIG. 1 and by block diagram in FIG. 2. Operation of the system is initiated by the sensing of a heart dysfunction in a victim 25. A heart dysfunction reader 26 reads or detects a sign such as a pulse, heart beat, electrical signals from the heart, or other sign which indicates operation or condition of the heart. A sensor 27 determines whether the sign read or detected by the heart dysfunction reader 26 shows a heart dysfunction indicating imminent or occurring cardiac arrest/sudden cardiac death (CA). If so, a signal from the sensor 27 is sent to loop processor 28. Loop processor 28 sends a signal to personal alarm 30 and also sends a signal to the locator broadcast initiator 31 which broadcasts an alarm signal to a location processor unit 32. The locator broadcast initiator 31 may also, depending upon its broadcast power and the respective distances to AED machines 33 and to an emergency response center 34, broadcast the alarm signal to the nearest AED machine alarms 35 and to the emergency response center 34. The broadcast alarm signal would activate an AED machine alarm 35 and an alarm at the emergency response center 34.

Personal alarm 30 is generally worn on the user and provides at least an audio alarm signal such as a loud alarm tone or siren and may also provide a visual signal such as a flashing light. To ensure that bystanders know what the personal alarm 30 means, a voice alarm such as a synthesized or recorded voice can be part of the alarm and announce that the user has just died from a heart attack and to get an AED machine. For example, the siren or tone could sound for a short time to attract attention to the user. The tone could then stop and the voice say "I am dead, get the AED". This sequence could be repeated as desired in any desired pattern. A person hearing or seeing the personal alarm can then become an emergency response person 36 and look for and obtain an AED machine 33 and return to the victim 25 to treat the victim. A reset switch, such as a push button switch, may be provided in connection with the personal alarm 30 or any portion of the system worn on or carried by the user so if the personal alarm starts to go off, indicating to the user that an alarm condition has been indicated, and the user can tell that the alarm is a false alarm, the user can reset the system and stop the alarm before it is sent. For this purpose, the system may be set up so that the personal alarm 30 is activated several seconds before the locator broadcast initiator 31 is activated to broadcast the alarm signal to give the user the opportunity to reset the system and silence the alarm signal if desired to do so by the user. For example, the user might inadvertently remove the heart dysfunction reader without deactivating the system first, or the heart dysfunction reader might be inadvertently knocked off or out of position during sleep or other activity of the user, which would result in the heart dysfunction reader reading a lack of sign or signal that the sensor would indicate as an alarm condition. In cases where the sensor is one that can determine imminent cardiac arrest/sudden cardiac death, a personal indicator is preferably provided to indicate along with the alarm that the alarm indicates imminent cardiac arrest/sudden cardiac death rather than actual cardiac arrest/sudden cardiac death so that the user does not reset or turn off the system just before cardiac arrest/sudden cardiac death occurs. Further, the user then knows to prepare for actual cardiac arrest/sudden cardiac death.

The AED machine alarm 35 is generally located on a portable AED machine 33 or on the case or bracket holding the AED machine 33 and, like the personal alarm 30, will provide at least an audio alarm such as a loud alarm tone or siren to alert anyone in the immediate area of the AED machine alarm 35 that there is a person at that time in immediate need of the machine. A visual alarm such as a flashing light to attract attention may also be used. An emergency response person 40 who hears the audio alarm or sees the visual alarm can then pick up the AED machine 33 and remove it from its holder or mounting bracket and attempt to find the victim 25. In attempting to find victim 25, the victim's personal alarm 30 indicates the location and identity of the victim 25. Thus, if the AED machine is in the immediate area of the victim 25, the emergency response person 40 with the AED machine can locate the victim by listening for and looking for the victim's personal alarm. Generally, the AED machine alarm 35 is not needed or desired once the AED machine 33 is obtained by the emergency response person 36 or 40 and such alarm would interfere with such emergency response person hearing the victim's personal alarm 30 and would be annoying in using the AED machine 33. The AED machine alarm 35 may be arranged to automatically go silent when the AED machine 33 is removed from its case or mounting bracket, or have a switch thereon that can be operated by an emergency response person 36 or 40 who obtains the machine to take to the victim 25. Further, the system could be arranged so that the victim's personal alarm 30 is relatively soft when initially activated and the AED machine alarm is relatively loud when initially activated and once the AED machine 33 is obtained by an emergency response person 36 or 40 and the AED machine alarm 35 is silenced, the victim's personal alarm 30 becomes relatively loud to help guide the emergency person to the victim's location.

The locator broadcast initiator 31, along with the loop processor 28 and personal alarm 30, are generally packaged together and worn by the user such as on a belt or strap, in a pocket, or otherwise. The heart dysfunction reader 26 and sensor 27 are also mounted on the user, such as on a wrist or on the chest, and the sensor may communicate with the loop processor 28 through wires or through wireless communication. Thus, the sensor 27 may include a low power wireless transmitter to transmit sensed alarm indications to the loop processor 28 which includes a receiver for receiving such signals. An example of a heart dysfunction reader that can be used is a heart rate monitor made by Polar that can be worn on the chest such as in a bra or with a strap or other attachment. All body mounted components could be mounted together, such as on a wristband with the heart dysfunction reader 26 being a wrist pulse detector. Further, there could be multiple heart dysfunction readers mounted on a user, each with its own sensor which communicates with the loop processor 28, or each sharing a single sensor communicating with the loop processor 28. FIG. 1, shows a chest mounted heart dysfunction reader 26 and sensor 27 and belt mounted loop processor 28, personal alarm 30, and locator broadcast initiator 31. An additional, redundant, heart dysfunction reader 26 and sensor 27 may also be mounted on the belt.

The system may or may not need or include the location processor unit 32. Its inclusion depends upon the broadcast range of the locator broadcast initiator 31 and the type of communication with the emergency response center 34 to be used. Because location broadcast initiator 31 is user worn and therefore will generally be limited to wireless communications and will normally be battery powered, the location processor unit 32 may be included to receive alarm signals from the locator broadcast initiator 31 at relatively close range to rebroadcast such alarm signals using a higher power and longer range transmitter, a cellular telephone transmitter, or a wire connection such as a connection to a conventional telephone system or a computer communication system. Location processor unit 32 may take various forms. It may be a portable unit to be moved or carried with the user to be located in close proximity to the user with a rechargeable battery and/or a unit which can be plugged into a standard AC wall outlet for power. It may be a mobile unit installed in a user's automobile. It may be a stationary unit installed by a user in his or her home or office, or units installed in various parts of public or private buildings or other places such as in parks or along highways to pick up alarm signals from a locator broadcast initiator 31. The location processing unit 32 then rebroadcasts the alarm signal or connects to and sends the alarm signal via a network such as a conventional or cellular telephone network or computer network to AED machine alarms 35 and to emergency response centers 34. Thus, the AED machine alarms 35 and the emergency response centers 34 may receive alarm signals from both the locator broadcast initiator 31 and the location processor unit 32. If communication is solely by a cellular telephone network, the locator broadcast initiator 31 may provide such cellular telephone communication without need for the location processor unit 32, or both the locator broadcast initiator 31 and the location processor unit 32 may provide cellular and other communication signals. An important aspect of the invention is to ensure response to cardiac arrest/sudden cardiac death as quickly as possible. Thus, redundancy in the system is encouraged and receipt from two sources of signals is a benefit.

Communication between the various system components such as between the locator broadcast initiator 31 and the location processing unit 32, and between either of these and the various alarms may use a variety of technologies. Various conventional wireless or wire technologies may be used as well as the wireless access protocol (WAP), X-10 and the newly developed Bluetooth system.

The personal alarm 30 associated with the victim 25 serves to provide location information regarding the victim 25 to those in the immediate area of the victim which are those who can hear the audio alarm from personal alarm 30 or see the visual alarm from personal alarm 30. If there is a person in the immediate area of the victim, that person can become an emergency response person 36 who then takes action to find an AED machine 33, aided by the audio and/or visual AED machine alarm 35 associated with the AED machine 33, and returns to treat the victim. If there is a person in the immediate area of the AED machine, that person can become an emergency response person 40 who hears or sees the AED machine alarm 35 and takes the AED machine 33 and finds the victim by hearing or seeing the victim's personal alarm 30. However, the AED machine generally will not be in the immediate area of the victim so the emergency response person 40 may have difficulty in finding the victim. Therefore, in transmitting the alarm signal to a remote site such as the emergency response center 34, or, in most cases an AED machine 33 which may be out of sight and earshot of the victim, it is desirable to transmit victim location information along with the alarm signals. For this purpose, it is desirable that the loop processor also provide victim location signals with the alarm signals or as the alarm signals for transmission to the emergency response center 34 and the AED machine alarms 35. Such victim location signals may be generated by and supplied by various sources. The purpose of the location signals is to provide information that can be used by an emergency response person 40 or 41 to easily locate the victim 25. Global positioning satellite (GPS) signals are supplied by satellites and are currently used to determine location of persons and objects. Such signals can be used to accurately determine the position of a person or object receiving the signals and various devices are currently available to be carried by a person or object such as a vehicle which receives the GPS signals and indicates the position of the receiver. For example, Alpine Electronics of America, Inc. of Torrance, Calif. manufactures and sells the Alpine DVD PowerNav System which provides a computer and display for a vehicle. When a destination is entered into the system, in this case the destination would be the location of the victim as indicated by the received location signals, the Alpine PowerNav system will display a map showing the route to the location and will provide audio instructions telling a person in the vehicle when to turn, in which direction to turn, and how far to go before turning to guide the person and vehicle to the desired location. Thus, with a victim location, the emergency response person can be guided to the victim. As another example, Magellan Corporation of San Dimas, Calif. manufactures and sells several models of hand held GPS guidance units which may be held by a user and which displays a map and directions for reaching a destination. With the victim's location entered into the device, the device could guide an emergency response person on foot or in a vehicle to the victim. The system of the invention will need to be configured to provide victim location information in a format that can be entered into the guidance units and the format required will depend upon the guidance unit used. The invention contemplates a dedicated guidance unit as part of the AED alarm 35 connected to the AED machine 33, which, as part of the reception of the alarm signal from the locator broadcast initiator 31 or the location processor unit 32, enters the location signals into the guidance unit as the desired location so that the guidance unit will immediately guide the emergency response person 40 to the victim. A similar unit can be used at the emergency response service for emergency response person 41.

With a GPS system, the loop processor 28 will generally merely take the GPS signals as received from GPS satellites, indicated generally as signals from the GPS satellites or other location signal generator 38, and pass them through to the locator broadcast initiator 31. With other types of locating systems, the loop processor 28, locator broadcast initiator 31, or location processor unit 32 may perform location calculations or do other signal processing, as necessary, in respect to signals received by it to generate signals indicative of the victim's location that are then transmitted to the AED alarm 35 and the emergency response center 34.

The loop processor 28 receives the alarm signal from the sensor 27 and location signals from the GPS satellites or other location signal generator 38 and combines them for transmission to the AED machine alarms 35, and to the emergency response center 34. The AED machine alarms 35 attract emergency response persons 40 to the AED machine to pick up the AED machine and take it to the location of the victim 25 for use. Similarly, the alarm at the emergency response center 34 causes dispatch of an emergency response person 41 from an emergency response service 42, such as a paramedic team, fire or police person, or other response person to the victim 25. Such emergency response person 41 will have an AED machine available to use when reaching the victim 25. The emergency response service 42 and the emergency response person 41 from the emergency response service may also have access to professional emergency support 43 which can take the form of a panel of heart specialists who are available for consultation by the emergency response person 41 during and after the emergency response to answer questions and direct the emergency response in case of unexpected or unusual problems. The location indicating equipment used in conjunction with the AED machine alarms 35 and by the emergency response center 34 may be a portable display with associated location indicating equipment as indicated above that receives the location signals from the location broadcast initiator 31 and/or location processor unit 32 and generates a map or other directions to indicate the location of the victim, or may merely indicate the location of the victim, such as by address, room number, office number, etc. The emergency response persons 40 and 41 can then follow the map or other indications, or just knowing the victim's location, can travel to the location of the victim 25. Once in close proximity to the victim 25, the victim's personal alarm 30 can more clearly identify the victim 25.

In some cases, rather than location signals such as GPS signals being broadcast with the alarm signals, other locating systems, such as cell phone positioning systems which are now becoming available, may be used. In such instance, the alarm signal is sent by the location processor unit 32 and/or the location broadcast initiator 31 to the emergency response service 34, and possibly to the AED machine alarms 35, via cell phone. The cell phone locating system then indicates the location of the cell phone, i.e., the location of processor unit 32 or locator broadcast initiator 31, where the cell call originated. Similarly, a 911 call positioning system which is also now becoming available in some areas, may be used to supply the position information.

While it is generally preferred to include location and guidance information with the AED machine alarms 35, depending upon the number and placement of AED machines 33 in an area, the AED machine alarms 35 may or may not include a location indicating capability. For example, if AED units are placed in most buildings in a geographic area or are located in a closed environment such as in an airplane where the victim's personal alarm 30 can be heard and used to identify the location of the victim 25 to an emergency response person with the AED, additional location indicating equipment is not necessary on the AED machine. However, where the victim's personal alarm 30 may not be heard by the emergency response person 40 or 41, additional location indicating equipment is generally desirable.

If desired, the system can include the capability to transmit medical record or other information about a victim when transmitting the alarm. In such instance, the person being sensed will enter and have stored in memory in the loop processor 28, at least relevant medical history information or other relevant information, such as emergency contact information, which would be helpful to an emergency response person 36, 40, or 41, or emergency response service 42 or professional emergency support 43, in treating and further follow-up of the victim. For example, information as to a victim's doctor and emergency contact person can be used to contact the doctor and make arrangements to follow-up with victim treatment once the emergency response person revives the victim, emergency contact information can be used to contact such person once the victim is revived or in the event the victim cannot be revived, or relevant medical information can be used by a paramedic or other medical professional emergency response person for follow-up care.

It is contemplated, and initial research work is currently being done at MIT on an example of such a network, referred to as The Oxygen Alliance, that a network will be developed using network sensors, receivers, and transmitters ubiquitously placed in buildings and other locations to sense the presence of persons and receive information from and transmit information to such persons and to remote locations such as computers. Such a network could be used as a locator unit or locator system 45 for a victim with information as to the victim's location being transmitted from a local network transmitter in a room or other nearby location to the loop processor 28 indicating the victim's location. These location signals would then be included as part of or with the alarm signals as previously indicated to provide victim location information to the emergency response person with the alarm. The network (locator unit 45) may include transmitters in every room of a building or on every floor or every wing of a building and in common areas to provide the location information to the victim's loop processor 28 wherever the victim might be within the extent of the network. Further, the network itself could provide the transmission system for the alarm and location information. In such case, the alarm signal would be transmitted to a receiver in the network and such signal, along with the location information generated by the network and, if desired, identification and medical history information from the loop processor or from network sources, is transmitted through the network to the emergency response center 34 and the AE machine alarms 35. The alarm and location information can be provided by the locator broadcast initiator 28 and location processor unit 32, and the network, each as a redundant back up system to the other. As contemplated by "The Oxygen Alliance," locator unit 45 can include a series of receivers and/or transmitters or communication devices (transceivers), wired or wireless, within public or private buildings or areas or anywhere a victim may be. The devices can be independent or interactively linked to a companion base station in order to generate the needed location and applicable information and retransmit the alarm signal as well as other applicable information. The devices will be placed in strategic locations, so as to pick up information regarding the location of the victim and desired identification information, such as personal medical history, and transmit such information to emergency response centers and AED machines located close to the victim. In this embodiment, the notification and alerting of emergency response persons takes place redundantly through the ubiquitous network sensors as well as through the transmission of signals in the system of the invention as previously described.

An example of a locator unit 45 using presently available technology includes a plurality of room mounted local address transmitters 50–59 each located in a different room of a building having eight rooms 60–68 and a hall 69, shown schematically in FIG. 3. Each transmitter 50–59 includes a transceiver such as a Bluetooth transceiver chip made by Motorola, Inc. along with a programmed location chip in which the location, in this case the building address and room number, is encoded. A loop processor 70 on a victim 71, who had a cardiac arrest/sudden cardiac death in room 62, also includes a Bluetooth transceiver chip which, through Bluetooth communications transmits an alarm signal as an enquiry signal to the Bluetooth transceiver in the local address transmitter 52 located in room 62. Upon recieving the enquiry signal from loop prossessor 70, local address transmitter 52 responds and transmits the address and room number as encoded in the address chip back to the loop processor 70, which, in turn, combines it, as the or part of the location information with the alarm signal as previously discussed and causes transmission (through the associated locator broadcast initiator and/or associated location processor unit as previously described)of the alarm signal and location signals to AED machine alarms 35 and the emergency response center 34.

A building map 75 located near the front door 76 of the building receives signals from either the locator broadcast initiator or location processing unit associated with loop processor 70 or from the local address transmitter 52, which then indicates, such as by a light in room 62 as shown on building map 75, or by displaying a room number on a display in conjunction with map 75, the location of the victim. Thus, an emergency response person entering the building can look at building map 75 and see from the map or the display therein the location of the victim 71.

The locator unit as described can be used alone to provide location signals or in addition to the GPS signals where the GPS signals can be used to guide the emergency response person to the building and the locator unit then indicate the location of the victim within the building. FIG. 3 is a simplified illustration of a building. The location unit's helpfulness or even necessity is apparent with a large, complex building or a multistory building, such as large office buildings, manufacturing plants, public or civic buildings, and sports arenas or stadiums.

In general, as indicated by the above example, the location unit of the example uniquely identifies the victim's location in complex buildings, places, or areas to enable an emergency response person to quickly identify the location beyond merely the general location or address of the victim as would be given by GPS signals. The system includes a location programable chip system that can receive and rebroadcast unique locations through the loop processor. This is accomplished by such additional circuitry as a Bluetooth compatible transceiver and would be powered by, but not limited to, a low voltage battery system. The locator unit can function independently or in network concert with other location units.

The unit may also incorporate an emergency signal if desired as well as having the capability of generating emergency signals directly to the AED and/or emergency response person described within the emergency loop.

The system of the invention will preferably be set up to conduct periodic self tests to insure that all system components are operating correctly and that the system components that communicate with outside systems, such as with cell phone networks and remote emergency response centers, are communicating and interfacing correctly. In case of a system malfunction, an alarm is given to the system user. The system should also include a low battery indicator.

It should be realized that the emergency response persons contemplated by the system of the invention are not necessarily medically trained or even previously trained in operation of the AED machine. The emergency response person as referred to herein is any person who obtains the alarm information regarding the victim through the system of the invention and then responds to such alarm information. Thus, such emergency response person is any person who is alerted by the personal alarm 30, the AED alarm 35, or alerted by the emergency response center 42 and responds.

The system of the invention can include special "buddy" alarms. Such alarms are alarms carried by one or more special "buddy" or "buddies", such as a spouse or friend who is generally near the person being sensed, so that that person or "buddy" is immediately alerted to a cardiac arrest/sudden cardiac death condition in the person being sensed and such "buddy" can then immediately become the emergency response person.

Where AED machines are located fairly close together so that the system of the invention activates the AED alarms on several AED machines, several emergency response persons may be activated, one for each machine, and all will begin the search for the victim. Again, this is part of the beneficial redundancy of the system and increases the chances of an emergency response person reaching the victim in time to treat the victim before permanent damage occurs. With multiple emergence response centers receiving the alarm signal, such center can communicate to determine which is in the best position to respond, or multiple emergency response persons could respond.

The system of the invention will probably find most use and acceptance by those people who are likely to suffer cardiac arrest/sudden cardiac death, i.e., those 400,000 incident congestive heart failure patients and five million prevalent patients. However, a goal of the system is to be available and used by anyone and provide protection to a much wider range of people.

The system of the invention is designed to provide a closed loop response system. When an emergency condition is sensed, the alarm signal goes from the victim to the various alarms to an emergency response person. The emergency response person then responds to the victim. The personal alarm and the alarm in the AED machine and response from those alarms constitute a local area response shown by arrow and box 47 in FIG. 1, while the response from the emergency response center 42 is generally, but not necessarily, a more remote response indicated merely as emergency response 48 in FIG. 1. In addition, the indication of communication interface signal in several places in FIG. 1 merely indicate and represent that there are various types of communication channels that can be used in transmitting the alarm signal and location signals to the various alarms. Thus, these represent wireless and wired systems.

While the system has been described in connection with sensing persons who are human beings, particularly people who may be prone to a cardiac arrest/sudden cardiac death condition, it should be understood that such system can also be used with animals, particularly pets who might be inclined to a cardiac arrest/sudden cardiac death condition. In such instance, the alarm may not be as universally transmitted, but may be limited to the pets owners in a manner similar to the "buddy" system. Also, in such instance, and for purposes of this application, such animals being sensed or considered as the person being sensed.

Whereas the invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. An emergency response system for detecting locating, and responding to a person in a cardiac arrest/sudden cardiac death condition, comprising:

a sensor to detect a cardiac arrest/sudden cardiac death condition in a person being sensed;

processor circuitry responsive to the sensor to produce an alarm signal;

a personal alarm responsive to the alarm signal to indicate to an emergency response person the cardiac arrest/sudden cardiac death condition in the person being sensed and to provide an indication at the location of the person being sensed to identify the person being sensed and that person's location;

at least one automatic external defibrillator (AED) machine, wherein the at least one AED machine includes an AED alarm indicator associated with the at least one AED machine; and a transmitter for transmitting the alarm signal from the processor circuitry to the AED alarm indicator to indicate to an emergency response person that a person is in need of the AED machine and that such emergency response person should take the AED machine and find the person being sensed in need of such machine.

2. An emergency response system according to claim 1, wherein the personal alarm produces an audio signal at the location of the person being sensed.

3. An emergency response system according to claim 2, wherein the audio signal includes spoken words relating to the person's condition.

4. An emergency response system according to claim 1, wherein the personal alarm produces a visual signal at the location of the person being sensed.

5. An emergency response system according to claim 1, wherein the personal alarm is worn by the person being sensed.

6. An emergency response system according to claim 1, wherein the AED alarm indicator provides an audio alarm.

7. An emergency response system according to claim 1, wherein the processor circuitry obtains location indicating signals which indicate the location of the person being sensed and the transmitter transmits such location indicating signals with the alarm signals, and the AED alarm indicator includes location indicating means responsive to the transmitted location indicating signals to provide an indication of the sensed person's location to the emergency response person taking the AED machine.

8. An emergency response system according to claim 7, wherein the location indicating signals are global positioning satellite (GPS) signals received by the processor circuitry at the location of the person being sensed, and the AED alarm indicator location indicating means provides location information obtained from the GPS signals to the emergency response person.

9. An emergency response system according to claim 8, wherein a receiver to receive transmitted alarm and location indicating signals from the transmitter is located at at least one emergency response center to alert the at least one emergency response center to send an emergency response person to the person being sensed.

10. An emergency response system according to claim 9, wherein the location indicating signals include signals received by the processor circuitry from at least one local transmitter in the vicinity of the person being sensed transmitting location information, and the GPS signals supplement such location information obtained from the at least one local transmitter.

11. An emergency response system according to claim 10, additionally including a location processor unit responsive to the alarm signal transmitted by the transmitter to retransmit the alarm and location signals.

12. An emergency response system according to claim 11, wherein the retransmission of the alarm and location signals includes retransmission through an existing communication system.

13. An emergency response system according to claim 10, wherein the at least one local transmitter is a plurality of transmitters positioned in different locations within an area, each with a unique address indicating its individual position in the area, and wherein the location indicating signals include the unique address of one of the local transmitters.

14. An emergency response system according to claim 13, wherein respective local transmitters of the plurality of local transmitters are positioned in different rooms of a building.

15. An emergency response system according to claim 13, wherein the local transmitters transmit location signals in response to enquiry signals from the processor circuitry.

16. An emergency response system according to claim 7, wherein the location indicating signals are signals received by the processor circuitry from at least one local transmitter in the vicinity of the person being sensed transmitting location information.

17. An emergency response system according to claim 16, wherein the at least one local transmitter is a plurality of transmitters positioned in different locations within an area, each with a unique address indicating its individual position in the area, and wherein the location indicating signals include the unique address of one of the local transmitters.

18. An emergency response system according to claim 17, wherein respective local transmitters of the plurality of local transmitters are positioned in different rooms of a building.

19. An emergency response system according to claim 18, wherein the local transmitters transmit location signals in response to enquiry signals from the processor circuitry.

20. An emergency response system according to claim 18, additionally including a location processor unit responsive to the alarm signal transmitted by the transmitter to retransmit the alarm and location signals.

21. An emergency response system according to claim 20, wherein the retransmission of the alarm and location signals includes retransmission through an existing communication system.

22. An emergency response system according to claim 1, additionally including an alarm reset operable by the person being sensed to stop operation of the alarm.

23. An emergency response system according to claim 22, additionally including delay means for delaying operation of the transmitter for a period of time after operation of the personal alarm sufficient to allow operation of the reset means, if desired, before transmission of the alarm signal.

24. An emergency response system according to claim 1, additionally including a transmitter for transmitting the alarm signal to a remote location wherein the processor obtains location, indicating signals which indicate the location of the person being sensed and the transmitter transmits such location signals with the alarm signals, and wherein a receiver to receive transmitted alarm and location signals from the transmitter is located at at least one emergency response center to alert the at least one emergency response center to send an emergency response person to the person being sensed.

25. An emergency response system according to claim 24, wherein the location indicating signals are global positioning satellite (GPS) signals received by the processor circuitry at the location of the person being sensed, and the receiver at the emergency response center provides sensed person location information obtained from the GPS signals to the emergency response person.

26. An emergency response system according to claim 25, wherein location indicating signals include signals received by the processor circuitry from at least one local transmitter in the vicinity of the person being sensed transmitting location information and such location information supplements the location information obtained from the GPS signals.

27. An emergency response system according to claim 24, wherein the location indicating signals are signals received by the processor circuitry from at least one local transmitter in the vicinity of the person being sensed transmitting location information.

28. An emergency response system according to claim 1, additionally including means allowing access to the person being sensed upon activation of the alarm.

29. An emergency response system according to claim 28, wherein the means allowing access to the person being sensed unlatches any doors which may restrict access to the person being sensed.

30. An emergency response system according to claim 1, additionally including means to turn on lights at the location of the person beings sensed upon activation of the alarm.

31. An emergency response system according to claim 1, additionally including a second alarm responsive to the alarm signal to be carried by a selected emergency response person to immediately alert the selected emergency response person of the sensed cardiac arrest/sudden cardiac death condition in the person being sensed.

32. An emergency response system according to claim 1, wherein the person being sensed is an animal.

33. An emergency response system according to claim 1, wherein both the personal alarm and the AED alarm include audio alarms, wherein both the personal alarm and the AED alarm have first and second volume settings, the second volume setting of each being of lesser volume than the first volume setting of each, and additionally including means activating the personal alarm initially at its second volume setting and the AED alarm at its first volume setting, and, when the AED machine is taken by the emergency response person, the AED alarm switches to its second volume setting and the personal alarm switches to its first volume setting.

34. An emergency response system for detecting, locating, and responding to a person in a cardiac arrest/sudden cardiac death condition, comprising:
a sensor to detect a cardiac arrest/sudden cardiac death condition in a person being sensed;
processor circuitry responsive to the sensor to produce an alarm signal;
a personal alarm responsive to the alarm signal to indicate to an emergency response person the cardiac arrest/sudden cardiac death condition in the person being sensed and to provide an indication at the location of the person being sensed to identify the person being sensed and that person's location;
a plurality of local transmitters positioned in different locations within an area in the vicinity of the person being sensed, each with a unique address indicating its individual position in the area and each transmitting such address information;
a transmitter for transmitting the alarm signal to a remote location along with a location indicating signal which indicates the location of the person being sensed, and wherein the location indicating signals include the unique address of one of the local transmitters and global positioning satellite (GPS) signals received by the processor circuitry at the location of the person being sensed; and
a receiver to receive transmitted alarm and location signals from the transmitter located at at least one emergency response center to alert the at least one emergency response center to send an emergency response person to the person being sensed, said receiver providing sensed person location information obtained from the local transmitter unique address and from GPS signals to the emergency response person.

35. An emergency response system according to claim 34, wherein respective local transmitters of the plurality of local transmitters are positioned in different rooms of a building.

36. An emergency response system according to claim 34, wherein the local transmitters transmit location signals in response to enquiry signals from the processor circuitry.

37. An emergency response system according to claim 34, additionally including a location processor unit responsive to the alarm signal transmitted by the transmitter to retransmit the alarm and location signals.

38. An emergency response system according to claim 37, wherein the retransmission of the alarm and location signals includes retransmission through an existing communication system.

39. An emergency response system according to claim 34, additionally including an alarm reset operable by the person being sensed to stop operation of the alarm.

40. An emergency response system according to claim 34, wherein the unique address of one of the local transmitters included in the location indicating signal is received from the local transmitter by the processor circuitry.

41. An emergency response system for detecting, locating, and responding to a person in a cardiac arrest/sudden cardiac death condition, comprising:
a sensor to detect a cardiac arrest/sudden cardiac death condition in a person being sensed;
processor circuitry responsive to the sensor to produce an alarm signal;
a personal alarm responsive to the alarm signal to indicate to an emergency response person the cardiac arrest/sudden cardiac death condition in the person being sensed and to provide an indication at the location of the person being sensed to identify the person being sensed and that person's location;
a plurality of local transmitters positioned in different locations within an area in the vicinity of the person being sensed, each with a unique address indicating its individual position in the area and each transmitting such address information;
a transmitter for transmitting the alarm signal to a remote location along with a location indicating signal which indicates the location of the person being sensed, and wherein the location indicating signals include the unique address of one of the local transmitters; and
a receiver to receive transmitted alarm and location signals from the transmitter located at at least one emergency response center to alert the at least one emergency response center to send an emergency response person to the person being sensed.

42. An emergency response system according to claim 41, wherein respective local transmitters of the plurality of local transmitters are positioned in different rooms of a building.

43. An emergency response system according to claim 41, wherein the local transmitters transmit location signals in response to enquiry signals from the processor circuitry.

44. An emergency response system according to claim 41, additionally including an alarm reset operable by the person being sensed to stop operation of the alarm.

45. An emergency response system according to claim 44, additionally including delay means for delaying operation of the transmitter for a period of time after operation of the personal alarm sufficient to allow operation of the reset means, if desired, before transmission of the alarm signal.

46. An emergency response system according to claim 41, wherein the unique address of one of the local transmitters included in the location indicating signal is received from the local transmitter by the processor circuitry.

47. An emergency response system according to claim 41, additionally including a location processor unit responsive to the alarm signal transmitted by the transmitter to retransmit the alarm and location signals.

48. An emergency response system according to claim 47, wherein the retransmission of the alarm and location signals includes retransmission through an existing communication system.

* * * * *